United States Patent [19]

Dobler et al.

[11] Patent Number: 4,999,437
[45] Date of Patent: Mar. 12, 1991

[54] PREPARATION OF ASCORBIC ACID 2-PHOSPHATE AND OF 5, 6-ISOPROPYLIDENEASCORBIC ACID AND POTASSIUM MAGNESIUM L-ASCORBATE 2-PHOSPHATE AS AN ADVANTAGEOUS SALT OF L-ASCORBIC ACID 2- PHOSPHATE

[75] Inventors: Walter Dobler, Heidelberg; Joachim Paust, Neuhofen; Roland Betz, Niederkirchen, all of Fed. Rep. of Germany

[73] Assignee: BASF Aktiengesellschaft, Ludwigshafen, Fed. Rep. of Germany

[21] Appl. No.: 486,755

[22] Filed: Mar. 1, 1990

[30] Foreign Application Priority Data

Mar. 21, 1989 [DE] Fed. Rep. of Germany ......... 909198

[51] Int. Cl.$^5$ ................................................ C07F 9/06
[52] U.S. Cl. .................................... 549/222; 549/221; 549/315
[58] Field of Search ......................... 549/221, 222, 315

[56] References Cited

U.S. PATENT DOCUMENTS 4,179,445 12/1979 Sieb et al. ................... 260/340.9 R

FOREIGN PATENT DOCUMENTS 2719303 11/1977 Fed. Rep. of Germany.

OTHER PUBLICATIONS

Tetrahedron, vol. 35 (1979), pp. 1483-1486, J. Jernow et al.

*Primary Examiner*—Cecilia Shen
*Attorney, Agent, or Firm*—Oblon, Spivak, McClelland, Maier & Neustadt

[57] ABSTRACT

Ascorbic acid 2-phosphate is prepared by reacting ascorbic acid or an ascorbic acid derivative with $POCl_3$ in the presence of a tertiary amine in a suitable aqueous solvent at from $-10°$ to $25°$ C. while maintaining a pH of about 8-13.5 with KOH during the entire phosphorylation reaction and then isolating the ascorbic acid 2-phosphate, by a process in which an aqueous solution of a magnesium compound is added to the reaction mixture obtained in the phosphorylation, without prior treatment with an ion exchanger, until the formation of crystalline $KMg\ PO_4$ is complete, the $KMgPO_4$ which is crystallized out is separated off, the resulting filtrate is evaporated down at a pH of from 6 to 11 and/or from 0.1 to 5 times the amount, based on the evaporated filtrate, of a lower primary alkanol or acetone is added and the stirred mixture is cooled until KCl has completely crystallized out, and the ascorbic acid phosphate is isolated in a conventional manner from the reaction solution obtained by separating off KCl and substantially freed from inorganic salts. It is particularly advantageous if the ascorbic acid 2-phosphate is isolated in the form of the novel potassium magnesium ascorbate 2-phosphate, which is also claimed.

The process is particularly advantageous if the ascorbic acid derivative used is 5,6-isopropylideneascorbic acid which has been obtained by reacting ascorbic acid with acetone in the presence of oleum. The process is particularly important for the preparation of L-ascorbic acid 2-phosphate.

10 Claims, No Drawings

PREPARATION OF ASCORBIC ACID 2-PHOSPHATE AND OF 5, 6-ISOPROPYLIDENEASCORBIC ACID AND POTASSIUM MAGNESIUM L-ASCORBATE 2-PHOSPHATE AS AN ADVANTAGEOUS SALT OF L-ASCORBIC ACID 2-PHOSPHATE

The present invention relates to a process for the preparation of mono- or diphosphates of ascorbic acid, in particular of L-ascorbic acid, and a particularly advantageous method for the preparation of the 5,6-isopropy-lideneascorbic acid required for this purpose. The present invention furthermore relates to potassium magnesium L-ascorbate 2-phosphate, by means of which L-ascorbic acid 2-phosphate can be particularly advantageously isolated.

L-ascorbic acid (vitamin C) forms a vital part of balanced human nutrition and inclusion of this vitamin in the diet has been recommended. However, vitamin C is the least stable vitamin in foods since it reacts extremely easily with atmospheric oxygen. It is known, for example, that ascorbic acid reacts rapidly with oxygen to give dehydroascorbic acid, a compound which, although retaining the full vitamin C activity, decomposes rapidly and irreversibly into compounds without vitamin C activity. Ascorbic acid is also decomposed at high temperatures by dehydration in an acidic medium. Thus, efforts to incorporate L-ascorbic acid directly into dough or bakery products which are to be subsequently baked have proven ineffective since only small amounts of the vitamin C activity of the L-ascorbic acid withstand cooking and baking at high temperatures. Regarding the use of vitamin C in the animal feed sector, it is also very important for the vitamin to be present in a very heat-stable form so that the vitamin loss during incorporation in the animal feed by extrusion and pelletizing is very small. Vitamin C has recently become important in fish farming and shrimp farming. It is known that ascorbic acid can be made more stable to oxygen and heat by converting it into suitable derivatives.

Ascorbic acid monophosphate has the following important advantages over free ascorbic acid:
(1) relatively high stability to oxidation,
(2) general bioavailability since it can be cleaved by phosphatases in vivo and in vitro to give ascorbic acid (this has been demonstrated, for example, in guinea pigs, broilers, piglets, Rhesus monkeys and fish),
(3) high heat stability and hence the possibility of processing in extruders and
(4) high stability to hydrolysis.

The preparation of vitamin C phosphate was first described by Cutolo and Larizza (cf. Gazz. Chim. Ital. 91 (1961), 964). The preparation starts from ascorbic acid or 5,6-isopropylideneascorbic acid, which is phosphorylated with $POCl_3$ in the presence of pyridine and a strong base in water.

Some modifications to this process were subsequently published in the literature, and it was long a matter of contention as to whether the product obtained is ascorbic acid 2-phosphate or 3-phosphate, until this question was clearly answered by Jernow (cf. Tetrahedron, 35 (1979), 1483 et seq.). Some of this work is described in the said publication (loc cit). The most advantageous process to date for the preparation of ascorbic acid 2-phosphate is the process described in German Laid-Open Application DOS 2,719,303.

The disadvantage of all stated processes is that they are suitable only for use on a small scale, since the working up described is much too expensive for an industrial procedure. The problem is that the desired product has to be separated off from a large excess of inorganic salts originating from the phosphorylation process. For example, in the process described in German Laid-Open Application DOS 2,719,303, the phosphorylation gives a reaction solution which contains about 4.5 equivalents of KCl and 1.8 equivalents of $K_3PO_4$, i.e. about 6 equivalents of organic salts together, per equivalent of desired product.

According to German Laid-Open Application DOS 2,719,303, this solution is first passed over an ion exchanger in order to exchange the potassium ions for hydrogen ions. Since the salt concentration (KCl, $K_3PO_4$, potassium isopropylidene-L-ascorbic acid 2-phosphate) is very high, the procedure must be carried out in great dilution so that ion exchange takes place completely. In an industrial process, the resulting large volumes give rise to high capital costs and enormous energy costs for evaporation. In the subsequent neutralization with MgO, a large excess of base is required since, in addition to the acid obtained as the product, it is also necessary to neutralize the total excess HCl and $H_3PO_4$. Moreover, it is difficult to separate off $Mg_3(PO_4)_2$ since it is obtained in very finely divided form and is extremely difficult to filter. Furthermore, some of the ascorbic acid phosphate is precipitated with the finely divided $Mg_3PO_4$ and is therefore lost.

In this process, the desired product is precipitated as an Mg salt with an alcohol, and it is necessary to choose the conditions so that the large amount of $MgCl_2$ which forms from MgO and HCl during the neutralization remains in solution. According to our investigations, it was not possible to obtain an ascorbic acid phosphate free of inorganic salts, in spite of thorough washing of the product with large amounts of aqueous ethanol. In order to obtain a pure product by this process, it was necessary to redissolve the Mg ascorbic acid phosphate, converted into the acidic form using an ion exchanger and to convert the product into a recrystallizable salt using an auxiliary base, such as cyclohexylamine. The product purified in this manner was then converted into the desired salt.

Such a process is inconvenient and uneconomical and involves large losses and is therefore unsuitable for industrial production.

It is an object of the present invention to make the working up of the reaction mixture obtained in the phosphorylation of ascorbic acid or ascorbic acid derivatives with $POCl_3$ in the presence of tertiary amines by the process of German Laid-Open Application DOS 2,719,303 so advantageous that the industrial production of ascorbic acid phosphate is possible by this method.

We have found that this object is achieved and that, surprisingly, the free phosphoric acid present in the reaction solution and some of the cations of the solution, which are present as $K_3PO_4$ at the pH of the reaction solution of 7 or higher, preferably from 11 to 13, can be removed in a simple manner in the presence of all reaction products (ascorbic acid derivatives, KCl, $K_3PO_4$) and auxiliary reagents (tertiary amine, such as pyridine) if a magnesium compound, preferably an aqueous solution of an Mg compound, is added to the reaction solution. Despite the high concentration of salts and solids, the phosphoric acid combines to form a sparingly soluble salt which has the composition KMgPO$_4$ and forms well defined crystals which can readily be filtered off from the reaction solution, while at the same time the pH decreases to 7-11, preferably 9.0-10.5. The reaction can be carried out at from 0° to 50° C., preferably at about 20° C. The KMgPO$_4$ obtained is very pure and can be used directly as a fertilizer salt. It is particularly advantageous to use magnesium chloride as the magnesium compound since in this case the potassium displaced by the magnesium is present as KCl, which is in any case already present in the reaction mixture.

It was very surprising that a sparingly soluble salt which has the composition KMgPO$_4$ is obtained in high purity and can be readily separated off by filtration is formed from a solution containing so many components.

It is a decisive advantage that, as a result of these measures, some of the salt load of the reaction mixture can be separated off in the form of a salt which can be used as a fertilizer, without substantial amounts of the desired product being coprecipitated. This permits an economical and environmentally compatible process, since the salt load of the wastewaters is greatly reduced in this manner.

Removal of the inorganic phosphate is furthermore a great advantage since, consequently, a smaller amount of ion exchange resin is required for separating off the potassium and subsequently less Mg base is required for neutralization and no poorly filterable Mg$_3$(PO$_4$)$_2$ is obtained during the neutralization.

The present invention therefore relates to a process for the preparation of ascorbic acid 2-phosphate by reacting ascorbic acid or an ascorbic acid derivative which has a group of the formula I

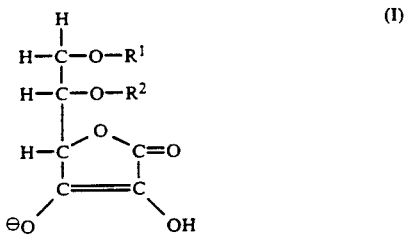

where R$^1$ and R$^2$ are each hydrogen or together form one of the groups

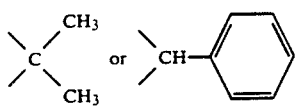

with POCl$_3$ in the presence of a tertiary amine in a suitable aqueous solvent at −10° to 25° C. while maintaining a pH of about 8-13.5, preferably 10-13, by adding KOH during the entire phosphorylation reaction, and then isolating the ascorbic acid 2-phosphate, wherein, to separate off the excess inorganic phosphate, about the stoichiometric amount of a magnesium compound, advantageously in the form of an aqueous solution, is added to the reaction mixture obtained in the phosphorylation, directly and without prior ion exchange treatment, at a pH >7, until the formation of crystalline KMgPO$_4$ is complete, the KMgPO$_4$ which has crystallized out is separated off and the ascorbic acid phosphate is isolated from the filtrate in a conventional manner.

The phosphorylation is advantageously carried out under the conditions described in German Laid-Open Application DOS 2,719,303.

In addition to ascorbic acid, suitable ascorbic acid derivatives which contain a group of the formula I

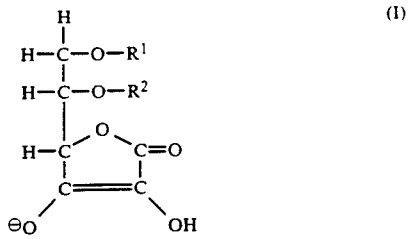

where R$^1$ and R$^2$ are each hydrogen or together form one of the groups

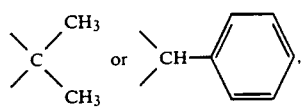

are the alkali metal salts or alkaline earth metal salts of ascorbic acid and its salts with a base-stable protective group at the carbon atom in the 6-position, for example 5,6-O-isopropylideneascorbic acid and 5,6-O-benzylideneascorbic acid. These compounds can be used in the four different stereoisomeric forms. The process is particularly important for the reaction of L-ascorbic acid and its derivatives.

Suitable tertiary amines are those which are miscible with the reaction mixture and are nonvolatile and have an ionization constant of less than about 10$^7$. Examples are lower trialkylamines, such as triethylamine, and cyclic amines, such as pyridine and α-, β- or γ-picoline. The best yields are obtained using pyridine. About 5 moles of the amine are used per mole of ascorbic acid.

The phosphorylation takes place particularly advantageously if the concentration of the amine in the reaction mixture is about 1.5-3, preferably 2.2-2.6, moles and that of the ascorbic acid is about 0.3-0.6, preferably 0.4-0.5, mole per liter.

An advantageously used solvent is water.

In general, the reaction temperature used should be the lowest temperature at which the reaction mixture remains liquid and at which the tertiary amine does not form a separate phase. Temperatures of from −10° to +10° C. are suitable.

Examples of suitable magnesium compounds are MgBr$_2$ and MgSO$_4$, and in particular magnesium chloride. It is advantageous to add the magnesium salt in the form of an aqueous solution.

The amount of magnesium salt is in general about 90-110 mol %, based on inorganic phosphate present in the reaction mixture.

The novel process is very advantageous if
(A) the starting material used is an ascorbic acid derivative which has a group of the formula I where R$^1$ and R$^2$ are each hydrogen or together form one of the groups

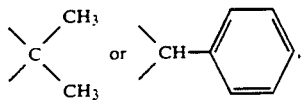

(B) an aqueous solution of a magnesium compound, preferably magnesium chloride, is added to the reaction mixture obtained in the phosphorylation, without prior treatment with an ion exchanger, until the formation of crystalline $KMgPO_4$ is complete, (C) the $KMgPO_4$ which is crystallized out is separated off, (D) to separate off the inorganic potassium salts the resulting filtrate is evaporated to a solids content of from 20 to 90, preferably from 40 to 50%, by weight at a pH of from 6 to 11, preferably from 7.5 to 8, and cooled to a temperature of from $-10°$ to $+20°$ C. until the potassium salts or potassium chloride have or has completely crystallized out, or the filtrate obtained after $KMgPO_4$ has crystallized out and been separated off is evaporated down at a pH of from 6 to 11, preferably from 7.5 to 8, and from 0.1 to 5, preferably from 0.8 to 1.2, times the amount, based on the filtrate used, of a lower primary alkanol or acetone is then added at from 0° to 60° C., preferably from 20° to 30° C., and the stirred mixture is cooled to a temperature of from $-20°$ to 20° C., preferably from 0° to 10° C., until the potassium salts or KCl have or has completely crystallized out, and (E) the ascorbic acid phosphate is isolated in a conventional manner from the reaction solution which is obtained by separating off the potassium salts or KCl and substantially freed from inorganic salts.

For further details of this isolation, reference may be made to, for example, German Laid-Open Application DOS 2,719,303.

The reaction mixture is advantageously brought to the suitable pH by adding KOH solution or HCl solution.

The tertiary amine, in particular pyridine, can readily be separated off and recovered from the condensate obtained in the evaporation in step E, and can be reused for the phosphorylation.

Examples of lower primary alkanols are the water-soluble alkanols of 1 to 4 carbon atoms, in particular methanol.

The alkanol is added in general at from 0° to 60° C., preferably from 20° to 30° C., and stirring and removal of the KCl is effected at from $-20°$ to 50° C., preferably from 0° to 10° C. The crystals are washed with alcohol or alcohol/water mixture and are then very pure and can be used for other purposes.

It is surprising that the isopropylideneascorbic acid phosphate, which is present as the potassium, dipotassium or tripotassium salt, remains completely in solution, especially when it is considered that the basic alkali metal and alkaline earth metal salts of ascorbic acid 2-phosphate are precipitated by the addition of alcohols.

It is a decisive advantage that a further part of the salt load can be separated off in the form of the useful salt. This is economical and environmentally compatible since the salt load of the wastewaters is reduced as a result. If the precipitated potassium salt is to be further used, and if it has to be a pure salt, magnesium chloride must be used as the magnesium compound.

Another considerable advantage is that a smaller amount of ion exchange resin is required for converting the potassium isopropylideneascorbic acid 2-phosphate into the acid form and no excess mineral acid is liberated during the ion exchange process.

Consequently, less Mg base is required for the neutralization too. A further advantage is that any base can be used in this procedure for neutralizing the ion exchange eluate which is free of mineral acid, since, in the subsequent crystallization, there is no longer any danger that inorganic salts will be precipitated together with the desired product. This is particularly advantageous if the cyclohexylammonium salt is to be prepared for subsequent ultrapurification, since this salt can then be prepared directly from the ion exchange eluate with the result that crystallization by the magnesium salt is superfluous.

The novel process is particularly advantageous if the starting material used is an ascorbic acid derivative which has a group of the formula I where $R^1$ and $R^2$ together form the group

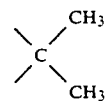

and which was prepared by treatment, for from 1 to 8, preferably from 5 to 6, hours at from $-20°$ to $+40°$ C., preferably from $-10°$ to $+10°$ C., with a mixture obtained by adding from 0 to 65, preferably about 20 to 30%, strength by weight oleum to acetone containing from 0 to 5, preferably from 0.6 to 1.5%, by weight of water at from $-30°$ to $+40°$ C., preferably from $-10°$ to 0° C., while stirring, separating off the crystallized 5,6-isopropylideneascorbic acid at about $-15°$ C. and pressing the crystals dry.

If the phosphorylation is carried out immediately afterward, the product which is crystallized out can be pressed dry without being washed and can be introduced, directly with the residual moisture present, into the aqueous KOH solution.

During the solution process, care should be taken to exclude oxygen.

The amount of oleum is chosen so that the sulfuric acid in the reaction mixture after the reaction is about 100-60, preferably about 80%, strength, based on the water content, the amount of water to be bound being calculated from the water content of the solvent and from the water formed in the reaction.

A stoichiometric amount of sodium hydroxide solution (preferably 40-50% strength) corresponding to the amount of acid is added, at from $-20°$ to $+40°$ C., preferably from $-10°$ to $+10°$ C., to the mother liquor of the crystals, which liquor now contains acetone, sulfuric acid and traces of ascorbic acid derivatives, $Na_2SO_4 \cdot nH_2O$ (n=3-5) being precipitated as a crystalline compound, which can be separated off by filtration. The acetone freed from the crystals can be distilled in good yield to give acetone which has a water content of about 1.4% and can be reused for the reaction described above. It is a considerable advantage that, using oleum as a catalyst, acetone having a water content of up to 5% can be used and a conversion of >99% still achieved. Oleum is very cheap.

It is a great advantage that the catalyst acid can be separated off completely in solid form as $Na_2SO_4$ after the reaction and hence acetone can be recovered from the mother liquor in high yield and high purity by filtration and simple distillation.

Because the 5,6-isopropylideneascorbic acid can be used directly in the phosphorylation, without washing, maximum yields are achieved.

It was very surprising that the reaction to give isopropylideneascorbic acid takes place in the manner described, without detectable formation of byproducts, although a large amount of sulfuric acid is present in the reaction mixture.

The result is a particularly advantageous overall process for the preparation of ascorbic acid 2-phosphate, in particular of L-ascorbic acid 2-phosphate, wherein (A) ascorbic acid, in particular L-ascorbic acid, is treated, at from $-10°$ to $+10°$ C. for from 5 to 6 hours, with a mixture obtained by adding from 0 to 65% strength by weight oleum to acetone containing from 0 to 5% by weight of water at from $-30°$ to $+40°$ C., while stirring, and the 5,6-isopropylidene-L-ascorbic acid which crystallizes out is separated off at about $-15°$ C., pressed dry and then reacted with $POCl_3$ while maintaining a pH of from 8 to 13.5 by means of KOH and in the presence of a tertiary amine at from $-10°$ to $+25°$ C. in a suitable aqueous solvent, (B) the aqueous solution of magnesium chloride is added to the reaction mixture obtained in the phosphorylation, without prior treatment with an ion exchanger, until the formation of crystalline $KMgPO_4$ is complete, (C) the $KMgPO_4$ which is crystallized out is separated off, (D) to separate off potassium chloride, the resulting filtrate is evaporated down at a pH of from 6 to 11, preferably from 7.5 to 8, and/or from 0.1 to 5, preferably from 0.8 to 1.2, times the amount, based on the evaporated filtrate, of a lower alkanol or acetone is added and the mixture is cooled to $0°-10°$ C. until KCl has completely crystallized out, and (E) the ascorbic acid phosphate or L-ascorbic acid phosphate is isolated in a conventional manner from the resulting reaction solution substantially freed from inorganic salts.

If the 5,6-isopropylideneascorbic acid prepared by reacting ascorbic acid (derivatives) and acetone in the presence of oleum is not to be further processed immediately but is to be dried and stored, the crystals must be washed repeatedly with ice cold acetone.

The present invention furthermore relates to a process for the preparation of 5,6-isopropylideneascorbic acid, wherein ascorbic acid is treated, at from $-20°$ to $+40°$ C., preferably from $-10°$ to $+10°$ C., for from 1 to 8, preferably from 5 to 6, hours, with a mixture obtained by adding from 0 to 65, preferably from 20 to 30%, strength by weight oleum to acetone containing from 0 to 5, preferably from 0.6 to 1.4%, by weight of water at from $-30°$ to $+40°$ C., preferably from $-10°$ to $+10°$ C., while stirring, and the 5,6-isopropylideneascorbic acid which crystallizes out is separated off at about $-15°$ C., if necessary, after washing with ice-cooled acetone.

The novel process is very particularly advantageous if the resulting ascorbic acid 2-phosphate is isolated via a potassium magnesium salt which has not yet been described. Potassium magnesium ascorbate 2-phosphate has very advantageous properties. It is precipitated from solutions in the form of well defined crystals and therefore has extremely good filtration properties and does not tend to agglomerate on drying. It has a defined content of water of crystallization and is not hygroscopic. Since, in contrast to the pure magnesium salt, it contains only 3 instead of 5 moles of water of crystallization per mole of ascorbate, the vitamin C content of such a dry powder is higher. A purer product, i.e. one which has been freed from bis-(2,2'-ascorbate) phosphate, is obtained on precipitating the ascorbic acid 2-phosphate as a calcium salt. However, the yields achievable here by crystallization are about 20% lower.

The present invention therefore also relates to the novel advantageous potassium magnesium ascorbate 2-phosphate. In this mixed salt, potassium and magnesium need not be present in an exactly stoichiometric ratio. The potassium/magnesium ratio in the solution from which the mixed salt is precipitated is identical to that of the crystalline product obtained therefrom. Optimum results are obtained in the isolation of ascorbic acid 2-phosphate in the form of a potassium/magnesium mixed salt if the salt has a composition of about $K_{1\pm0.3}Mg_{1\pm0.15}$ ascorbate 2-phosphate. The byproduct bis-(2,2'-ascorbate) phosphate crystallizes out in the K/Mg mixed salt in the same ratio as in the pure magnesium salt.

To isolate the ascorbic acid 2-phosphate in the form of the K/Mg mixed salt, in general the aqueous reaction solution which is obtained after the inorganic potassium salts have been separated off and which has been substantially freed from inorganic salts is passed over a moderately acidic cation exchanger, if necessary after removal of the lower alkanol or acetone used for precipitating KCl, and dilution with water, and MgO, $Mg(OH)_2$ or $MgCO_3$ is introduced into the resulting acidic eluate with cooling until the pH has increased to 7. The reaction solution obtained is then stirred for about 4 to 10, preferably 5 to 7, hours, stirred to remove suspended particles, evaporated down in a rotary evaporator and finally stirred into excess lower alkanol, preferably methanol, oracetone. This gives individual crystals which can readily be filtered. These crystals can easily be dried under nitrogen in a drying oven.

The present invention accordingly also relates to the process, described above, for the preparation of L-ascorbic acid 2-phosphate in the form of potassium magnesium L-ascorbate 2-phosphate, wherein (A) L-ascorbic acid is treated, at from $-10°$ to $+10°$ C. for from 5 to 6 hours, with a mixture obtained by adding from 0 to 65% strength by weight oleum to acetone containing from 0 to 5% by weight of water at from $-30°$ to $+40°$ C. while stirring, the 5,6-isopropylidene-L-ascorbic acid which crystallizes out is separated off at about $-15°$ C., pressed dry and then reacted with $POCl_3$ while maintaining a pH of from 8 to 13.5 by means of KOH and in the presence of a tertiary amine at from $-10°$ to $+25°$ C. in a suitable aqueous solvent, (B) an aqueous solution of magnesium chloride is added to the reaction mixture obtained in the phosphorylation, without prior treatment with an ion exchanger, until the formation of crystalline $KMgPO_4$ is complete, (C) the $KMgPO_4$ which is crystallized out is separated off, (D) to separate off potassium chloride the resulting filtrate is evaporated down at a pH of from 6 to 11 and/or from 0.1 to 5, preferably from 0.8 to 1.2, times the amount, based on the filtrate which may have been evaporated down, of a lower alkanol or acetone is added and the mixture is cooled to 0°-10° C. until KCl has completely crystallized out, (E) the resulting reaction solution which has been substantially freed from inorganic salts is treated with a moderately acidic cation exchanger which loses its exchange capacity at a pH of from about 2.0 to 0.5, preferably from 1.2 to 0.8, and (F) the L-ascorbic acid 2-phosphate is precipitated in the form of the novel potassium magnesium ascorbate 2-phosphate from the resulting reaction mixture essentially containing the monopotassium salt of L-ascorbic acid 2-phosphate, by adding MgO, Mg(OH)$_2$ or MgCO$_3$ until the solution has a pH of about 7 and if necessary treating the solution with methanol or acetone.

Moderately acidic cation exchangers which lose their exchange capacity at a pH of from about 2.0 to 0.5 are understood as being essentially gel-like or macroporous exchange resins which consist of a copolymer of styrene and divinylbenzene and carry suitable covalently bonded functional groups.

Particularly suitable functional groups are the following groups:

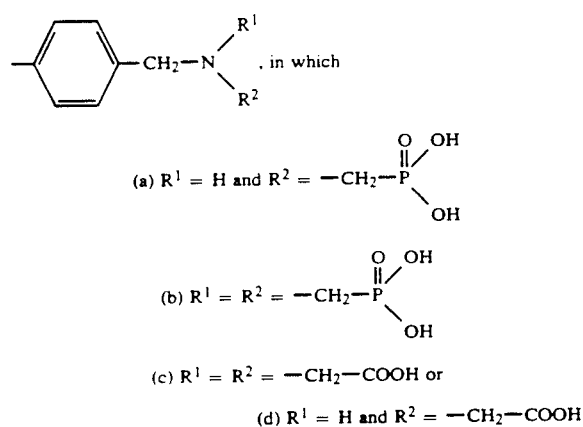

(a) $R^1 = H$ and $R^2 = -CH_2-P(=O)(OH)_2$ (b) $R^1 = R^2 = -CH_2-P(=O)(OH)_2$ (c) $R^1 = R^2 = -CH_2-COOH$ or (d) $R^1 = H$ and $R^2 = -CH_2-COOH$ In addition to the special resins, it is also possible to use other resins if they have a similar composition, i.e. if they carry the stated functional groups or functional groups having the same action. In comparison, exchange resins which carry only —COOH groups are not sufficiently acidic and those which carry —SO$_3$H groups are too acidic.

Examples are Lewatit OC1060 and Lewatit TP 207 and TP 208.

Lewatit OC 1060, which no longer has a measurable exchange capacity at a pH of about 0.5 is particularly suitable. This ensures that only 2 of the 3 K$^+$ ions in the potassium salt of the ascorbic acid 2-phosphate are exchanged. This is a particular advantage if it is intended to prepare potassium magnesium L-ascorbate 2-phosphate, since in this way K$^+$ is removed only in an amount which is subsequently to be replaced by Mg$^{2+}$.

In this reaction procedure, the reaction time for eliminating the isopropylidene protective group is about 2 hours at 30° C.

The great advantage of the use of moderately acidic ion exchangers compared with the use of strongly acidic ion exchangers in known processes is that the eluate formed is less acidic and the ascorbic acid 2-phosphate therefore does not undergo cleavage to form ascorbic acid again, which has a very advantageous effect on the product quality, in particular the color of the product. Further advantages of the procedure using the novel potassium magnesium L-ascorbate 2-phosphate are:

(a) smaller consumption of MgO
(b) lower salt emission
(c) better space-time yield because regeneration times for the ion exchanger are reduced by ⅓.

Neutralization of the resulting eluate with MgO, Mg(OH)$_2$ or MgCO$_3$ is carried out in general at from 20° to 25° C. To precipitate the potassium magnesium ascorbate 2-phosphate, the reaction solution is generally evaporated down and then advantageously poured into a lower alkanol or acetone, preferably into methanol.

With the aid of the novel process, it is possible to prepare the desired ascorbic acid 2-phosphates, in particular L-ascorbic acid 2-phospate, as such or in the form of its salts, in particular the novel potassium magnesium ascorbate 2-phosphate and 5,6-isopropylideneascorbic acid which can be used as an intermediate, industrially in a very advantageous manner.

EXAMPLE 1 A. Preparation of 5,6-isopropylidene-L-ascorbic acid 43 g of 24% strength oleum were added dropwise to 480 ml of acetone (water content about 0.4%). 120 g of L-ascorbic acid were introduced into the resulting mixture at 0° C., and the reaction mixture was stirred for 6 hours (h) at 0° C. It was then cooled to −15° C. and the crystals were filtered off under suction. The resulting filter cake was pressed dry and then further processed as described in B.

The yield was from 97 to 98% of theory, and the content of unconverted L-ascorbic acid was <0.5%.

B. Phosphorylation of 5,6-isopropylidene-L-ascorbic acid

The filter cake which was obtained according to A and pressed dry was slowly introduced into a mixture of 1200 ml of water and 300 ml of pyridine, the pH being kept at 12-13 by continuously adding KOH solution.

Thereafter, 146 g of POCl$_3$ were slowly added to the mixture at 0° C., the pH being kept at 13 by adding KOH. Stirring was then continued for a further 30 minutes (min) and the reaction mixture was tested for starting material.

C. Precipitation of KMgPO$_4$.6H$_2$O 70 g of MgCl$_2$.6H$_2$O in the form of an approximately 30% strength by weight aqueous solution were added to the reaction mixture obtained in B, and stirring was then carried out for a further hour. The crystalline precipitate formed was then filtered off under suction and the precipitate was washed with twice 100 ml of water and dried. 90 g of KMgPO$_4$.6H$_2$O were obtained in this manner.

D. Precipitation of KCl

The filtrate obtained in C was evaporated down to 1000 ml, after which 1 l of methanol was added. Stirring was then carried out for 1 h, after which the precipitate formed was filtered off under suction, washed twice with 200 ml of 60:40 methanol/water and dried. About 235 g of KCl were obtained.

E. Isolation of L-ascorbic acid phosphate as the magnesium salt

The combined filtrates from D were evaporated to about 800 g under reduced pressure and then passed over a column filled with a strongly acidic ion exchanger (Lewatit S-100 in the H+ form). Elution was then carried out using about 1 l of water, and about 2,200 ml of the acidic eluate were collected. About 39 g of MgO were added to the acidic eluate and the mixture was stirred until virtually everything had dissolved. The pH of the solution was about 8.5–9. A small amount of undissolved material was then filtered off, and the filtrate was evaporated to about 500 g. The solution thus obtained was added dropwise to about 1200 g of methanol, while stirring. The crystals formed were filtered off under suction, washed with 300 ml of methanol, pressed dry and dried. 210 g of magnesium L-ascorbate 2-phosphate.5H$_2$O were obtained in this manner. The product contained about 7% of 2,2'-bisascorbic acid monophosphate and had a vitamin C contnet of about 46%.

The yield was 80% of theory, based on vitamin C used.

EXAMPLE 2

The procedure described in Example 1A, B and C was followed. To precipitate KCl, the filtrate obtained according to 1C was evaporated to about 600 ml and then stirred for 1 h at 0° C. The precipitate formed was then filtered off under suction, washed twice with 200 ml of ice water and dried. About 185 g of KCl were obtained.

To isolate the L-ascorbic acid 2-phosphate as a magnesium salt, the combined filtrates were passed over a strongly acidic ion exchanger (Lewatit S-100 in the H+ form). Elution was then carried out with 1.5 liters of water, and about 2700 ml of the acidic eluate were collected. The eluate was brought to a pH of 9 with MgO. The small amount of undissolved material was then filtered off, and the solution was evaporated to about 600 ml.

This solution was then added dropwise to 1200 ml of methanol. The crystals formed were filtered off under suction and washed with 5 times 500 ml of a mixture of 1:1 methanol/water and once with 300 ml of methanol.

190 g of magnesium L-ascorbate 2-phosphate were obtained in this manner. The resulting product contained about 3% of 2,2'-bis-L-ascorbic acid monophosphate and had a vitamin C content of about 42%.

EXAMPLE 3 Preparation of 5,6-isopropylidene-L-ascorbic acid 55 g of 24% strength oleum were added dropwise to 480 ml of acetone (water content about 1.4%) at −10° C. 120 g of L-ascorbic acid were introduced into the resulting mixture at about 0° C., and the reaction mixture was stirred for 6 h at 0° C. It was then cooled to −15° C. and the crystals formed were filtered off under suction. The resulting filter cake was pressed dry, washed with twice 100 ml of ice cold acetone and dried at room temperature under reduced pressure from a water pump.

The yield was 97% of theory.

EXAMPLE 4

The procedure described in Example 1A, 1B, 1C and 1D was followed.

To isolate ascorbic acid 2-phosphate in the form of the novel potassium magnesium ascorbate 2-phosphate, the combined filtrates from 1D were evaporated to about 800 g under reduced pressure, diluted with 200 ml of water and then passed over a column filled with the moderately acidic ion exchanger Lewatit OC-1060 (polymeric amido-phosphonic acid, H+ form).

The eluate obtained had a pH of about 1.2. To eliminate the isopropylidene protective group, the eluate was kept at 30° C. for 2 h and then neutralized with MgO at from 20° to 25° C., stirred for a further 6 h, filtered and then evaporated to about 450 g in a rotary evaporator at 80° C. and thereafter immediately poured into 1100 ml of methanol. The salt which crystallized out was filtered off, washed with methanol and dried.

220 g of individual corn-yellow crystals were obtained, corresponding to a yield of 87.7% of theory, based on ascorbic acid.

Analysis of the salt gave an atomic ratio of K$_{0.8}$Mg$_{1.06}$C$_{5.6}$H$_{12.8}$P$_1$, corresponding to the compound KMgC$_6$H$_6$PO$_9$.3H$_2$O.

According to HPLC analysis, the product contained 89.0% of ascorbate 2-phosphate and 9.9% of bis-(2,2'-ascorbate) phosphate.

EXAMPLE 5

To demonstrate the advantageous properties of the novel potassium magnesium L-ascorbate 2-phosphate compared with potassium L-ascorbate 2-phosphate and magnesium L-ascorbate 2-phosphate, the filtration resistance, the agglomeration on drying and the dust formation of potassium magnesium L-ascorbate 2-phosphates of the formula K$_x$Mg$_y$C$_6$H$_6$PO$_9$.3H$_2$O, i.e. of potassium magnesium L-ascorbate 2-phosphates having different K/Mg ratios, were compared with the corresponding properties of the potassium salts (x=3, y=0) or magnesium salts (x=0, y=1.5).

| Experiment | X | Y | Filtration resistance | Agglomeration on drying | Dust formation |
|---|---|---|---|---|---|
| a) | 0.00 | 1.50 | +++ | +++ | +++ |
| b) | 0.08 | 1.46 | +++ | +++ | +++ |
| c) | 0.17 | 1.42 | +++ | ++ | ++ |
| d) | 0.27 | 1.37 | ++ | ++ | ++ |
| e) | 0.36 | 1.32 | ++ | + | ++ |
| f) | 0.48 | 1.26 | + | + | + |
| g) | 0.61 | 1.20 | − | − | + |
| h) | 0.75 | 1.12 | − | − | + |
| i) | 0.83 | 1.09 | − | − | + |
| j) | 1.08 | 0.96 | − | − | + |
| k) | 1.20 | 0.86 | − | − | + |
| l) | 1.54 | 0.73 | + | + | − |
| m) | 1.86 | 0.57 | + | + | − |
| n) | 2.15 | 0.43 | + | ++ | − |
| o) | 3.00 | 0.00 | Product obtained as an oil | | |

The experiments showed that salts having the composition K$_{1\pm0.3}$Mg$_{1\pm0.15}$ ascorbate 2-phosphate have the best product properties.

Evaluation scale:
+++ Very great
++ Great
+ Average
− Low

We claim:
1. A process for the preparation of ascorbic acid 2-phosphate by reacting ascorbic acid or an ascorbic acid derivative which has a group of the formula I

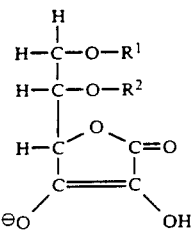 (I)

where $R^1$ and $R^2$ are each hydrogen or together form one of the groups

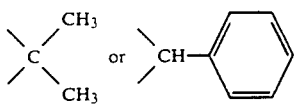

with $POCl_3$ in the presence of a tertiary amine in a suitable aqueous solvent at $-10°$ to $25°$ C. while maintaining a pH of about 8-13.5, by adding KOH during the entire phosphorylation reaction, and then isolating the ascorbic acid 2-phosphate, wherein, to separate off the excess inorganic phosphate, about the stoichiometric amount of a magnesium compound, advantageously in the form of an aqueous solution, is added to the reaction mixture obtained in the phosphorylation, directly and without prior treatment with an ion exchanger, at a pH > 7, until the formation of crystalline $KMgPO_4$ is complete, the $KMgPO_4$ which is crystallized out is separated off and the ascorbic acid phosphate is isolated from the filtrate in a conventional manner.

2. A process for the preparation of ascorbic acid 2-phosphate as claimed in claim 1, wherein
   (A) the starting material used is an ascorbic acid derivative which has a group of the formula I where $R^1$ and $R^2$ are each hydrogen or together form one of the groups

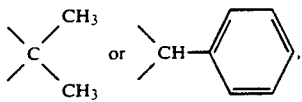

(B) an aqueous solution of a magnesium compound is added to the reaction mixture obtained in the phosphorylation, without prior treatment with an ion exchanger, until the formation of crystalline $KMgPO_4$ is complete,
   (C) the $KMgPO_4$ which is crystallized out is separated off,
   (D) to separate off the inorganic potassium salts, the resulting filtrate is evaporated to a solids content of from 20 to 90% by weight at a pH of from 6 to 11 and cooled to a temperature of from $-10°$ to $+20°$ C. until the potassium salts have completely crystallized out, and
   (E) the ascorbic acid phosphate is isolated in a conventional manner from the reaction solution which is obtained by separating off the inorganic potassium salts and substantially freed from inorganic salts.

3. A process for the preparation of ascorbic acid 2-phosphate as claimed in claim 1, wherein
   (A) the starting material used is an ascorbic acid derivative which has a group of the formula I where $R^1$ and $R^2$ together form one of the groups

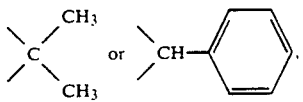

(B) an aqueous solution of a magnesium compound is added to the reaction mixture obtained in the phosphorylation, without prior treatment with an ion exchanger, until the formation of crystalline $KMgPO_4$ is complete,
   (C) the $KMgPO_4$ which is crystallized out is separated off,
   (D) to separate off the inorganic potassium salts, the resulting filtrate is evaporated down at from $0°$ to $60°$ C. and at a pH of from 6 to 11, and from 0.1 to 5 times the amount, based on the evaporated filtrate, of a lower primary alkanol or acetone is added and the stirred mixture is cooled to a temperature of from $-20°$ to $+50°$ C. until the potassium salts have completely crystallized out, and
   (E) the ascorbic acid phosphate is isolated in a conventional manner from the reaction solution which is obtained by separating off the inorganic potassium salts and substantially freed from inorganic salts.

4. A process for the preparation of ascorbic acid 2-phosphate as claimed in claim 1, wherein the starting material used is an ascorbic acid derivative which has a group of the formula I where $R^1$ and $R^2$ together form the group

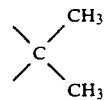

and which was prepared by treatment, for from 1 to 8 hours at from $-20°$ to $+40°$ C., with a mixture obtained by adding from 0 to 65% strength by weight oleum to acetone containing from 0 to 5% by weight of water at from $-30°$ to $+40°$ C. while stirring, separating off the 5,6-isopropy-lideneascorbic acid which crystallizes out, at about $-15°$ C., and pressing the crystals dry.

5. A process for the preparation of L-ascorbic acid 2-phosphate as claimed in claim 1, wherein
   (A) L-ascorbic acid is treated, at from $-10°$ to $+10°$ C. for from 5 to 6 hours, with a mixture obtained by adding from 0 to 65% strength by weight oleum to acetone containing from 0 to 5% by weight of water at from $-30°$ to $+40°$ C., while stirring, and the 5,6-isopropy-lidene-L-ascorbic acid which crystallizes out is separated off at about $-15°$ C., pressed dry and then reacted with $POCl_3$ while maintaining a pH of from 8 to 13.5 and in the presence of a tertiary amine at from $-10°$ to $+25°$ C. in a suitable aqueous solvent,
   (B) the aqueous solution of magnesium chloride is added to the reaction mixture obtained in the phosphorylation, without prior treatment with an ion exchanger, until the formation of crystalline $KMgPO_4$ is complete,
   (C) the $KMgPO_4$ which is crystallized out is separated off, (D) to separate off potassium chloride, the resulting filtrate is evaporated to a solids content of from 20 to 90% by weight at a pH of from 7 to 11 and cooled to a temperature of from −20° to +20° C. until KCl has completely crystallized out, and (E) the L-ascorbic acid phosphate is isolated in a conventional manner from the reaction solution obtained by separating off KCl and substantially freed from inorganic salts.

6. A process for the preparation of L-ascorbic acid 2-phosphate as claimed in claim 1, wherein (A) L-ascorbic acid is treated, at from −10° to +10° C. for from 5 to 6 hours, with a mixture obtained by adding from 0 to 65% strength by weight oleum to acetone containing from 0 to 5% by weight of water at from −30° to +40° C., while stirring, and the 5,6-isopropy-lidene-L-ascorbic acid which crystallizes out is separated off at about −15° C., pressed dry and then reacted with $POCl_3$ while maintaining a pH of from 8 to 13.5 by means of KOH and in the presence of a tertiary amine at from −10° to +25° C. in a suitable aqueous solvent, (B) the aqueous solution of magnesium chloride is added to the reaction mixture obtained in the phosphorylation, without prior treatment with an ion exchanger, until the formation of crystalline $KMgPO_4$ is complete, (C) the $KMgPO_4$ which is crystallized out is separated off, (D) to separate off potassium chloride, the resulting filtrate is evaporated down at a pH of from 6 to 11, and from 0.1 to 5, preferably from 0.8 to 1.2, times the amount, based on the evaporated filtrate, of a lower alkanol or acetone is added and the mixture is cooled to 0°–10° C. until KCl has completely crystallized out, and (E) the L-ascorbic acid phosphate is isolated in a conventional manner from the resulting reaction solution substantially freed from inorganic salts.

7. A process for the preparation of L-ascorbic acid 2-phosphate as claimed in claim 1, wherein (A) L-ascorbic acid is treated, at from −10° to +10° C. for from 5 to 6 hours, with a mixture obtained by adding from 0 to 65% strength by weight oleum to acetone containing from 0 to 5% by weight of water at from −30° to +40° C. while stirring, the 5,6-isopropylidene-L-ascorbic acid which crystallizes out is separated off at about −15° C., pressed dry and then reacted with $POCl_3$ while maintaining a pH of from 8 to 13.5 by means of KOH and in the presence of a tertiary amine at from −10° to +25° C. in a suitable aqueous solvent, (B) an aqueous solution of magnesium chloride is added to the reaction mixture obtained in the phosphorylation, without prior treatment with an ion exchanger, until the formation of crystalline $KMgPO_4$ is complete, (C) the $KMgPO_4$ which is crystallized out is separated off, (D) to separate off potassium chloride the resulting filtrate is evaporated down at a pH of from 6 to 11 and/or from 0.1 to 5, preferably from 0.8 to 1.2, times the amount, based on the filtrate a lower alkanol or acetone is added and the mixture is cooled to 0°–10° C. until KCl has completely crystallized out, (E) the resulting reaction solution which has been substantially freed from inorganic salts is treated with a moderately acidic cation exchanger which loses its exchange capacity at a pH of from about 2.0 to 0.5, and (F) the L-ascorbic acid 2-phosphate is precipitated in the form of the novel potassium magnesium ascorbate 2-phosphate from the resulting reaction mixture essentially containing the monopotassium salt of L-ascorbic acid 2-phosphate, by adding MgO, $Mg(OH)_2$ or $MgCO_3$ until the solution has a pH of about 7 and if necessary treating the solution with methanol or acetone.

8. Potassium magnesium L-ascorbate 2-phosphate.

9. $K_{1\pm0.3}Mg_{1\pm0.15}$ L-ascorbate 2-phosphate.

10. A process for the preparation of 5,6-isopropylideneascorbic acid by reacting ascorbic acid with acetone, wherein the ascorbic acid is treated, at from −10° to +10° C. for from 5 to 6 hours, with a mixture obtained by adding from 0 to 65% strength by weight oleum to acetone containing from 0 to 5% by weight of water at from −30° to +40° C. while stirring, and the 5,6-isopropy-lideneascorbic acid which crystallizes out is separated off at about −15° C., if necessary after washing with ice-cooled acetone.

* * * * *

UNITED STATES PATENT AND TRADEMARK OFFICE
CERTIFICATE OF CORRECTION

PATENT NO. : 4,999,437
DATED : March 12, 1991
INVENTOR(S) : Walter Dobler et al.

It is certified that error appears in the above-identified patent and that said Letters Patent is hereby corrected as shown below:

On the title page, in item [30]:
  The Foreign Application Priority Data is incorrect, should be, --Mar. 21, 1989 [DE] Fed. Rep. of Germany ......3909198--.

Signed and Sealed this

Third Day of November, 1992

Attest:

DOUGLAS B. COMER

Attesting Officer

Acting Commissioner of Patents and Trademarks